US005703225A

United States Patent [19]

Shet et al.

[11] Patent Number: 5,703,225
[45] Date of Patent: Dec. 30, 1997

[54] SULFONATED CELLULOSE HAVING IMPROVED ABSORBENT PROPERTIES

[75] Inventors: Ramakant Tukaram Shet, Neenah; Palani Raj R. Wallajapet, Wauwatosa, both of Wis.

[73] Assignee: Kimberly-Clark Worldwide, Inc., Neenah, Wis.

[21] Appl. No.: 571,332

[22] Filed: Dec. 13, 1995

[51] Int. Cl.$^6$ .............. C08B 5/00; A61F 13/15; A61F 13/20; F26B 13/26

[52] U.S. Cl. .............. 536/59; 536/56; 34/95; 604/358

[58] Field of Search .............. 536/59, 56; 34/95; 604/358

[56] References Cited

U.S. PATENT DOCUMENTS

| | | | |
|---|---|---|---|
| 1,846,093 | 2/1932 | Dils. | |
| 3,567,708 | 3/1971 | Manning et al. | 536/59 |
| 4,082,743 | 4/1978 | Hearon et al. | 536/30 |
| 4,141,746 | 2/1979 | Schweiger | 536/59 |
| 4,242,506 | 12/1980 | Schweiger | 536/59 |
| 4,409,289 | 10/1983 | Menault et al. | 428/374 |
| 4,708,771 | 11/1987 | Beaulieu | 162/83 |
| 4,818,598 | 4/1989 | Wong | 428/284 |
| 4,872,983 | 10/1989 | Diamantoglou et al. | 210/500.29 |
| 5,008,385 | 4/1991 | Diamantoglou | 536/56 |
| 5,089,089 | 2/1992 | Beaulieu | 162/234 |
| 5,550,189 | 8/1996 | Qin et al. | 525/54.3 |
| 5,552,967 | 9/1996 | Shet | 162/9 |

FOREIGN PATENT DOCUMENTS

| | | | |
|---|---|---|---|
| 0 172 135 A1 | 2/1986 | European Pat. Off. | D21C 3/22 |
| 0 210 756 A2 | 2/1987 | European Pat. Off. | A61L 15/00 |
| 0 319 862 A2 | 6/1989 | European Pat. Off. | B01D 13/04 |
| 0 685 593 A2 | 12/1995 | European Pat. Off. | D21C 9/00 |
| 1 057 440 | 5/1959 | Germany | 162/157.6 |
| 1 546 877 | 5/1979 | United Kingdom | D21C 3/06 |
| WO 95/11925 A1 | 5/1995 | WIPO | C08B 15/00 |

OTHER PUBLICATIONS

Patent Abstracts of Japan, vol. 016, No. 425, (C–0982), Sep. 7, 1992, JP 04–146901 A, (OJI Paper Co. Ltd.), May 20, 1992.

Allan, G. G. and Reif, W. M., "Fiber Surface Modification," *Svensk Papperstidning*, arg 74, Sep. 30, 1971, pp. 563–570.

Anderson, R., "Relation Between Compression Stiffness and Costs for Wet Stiff Corrugated Boards," *Svensk Papperstidning*, Nr. 7, 1976, pp. 212–214.

Stamm, A. J., "Dimensional Stabilization of Paper by Catalyzed Heat Treatment and Cross–Linking with Formaldehyde," *TAPPI*, vol. 42, No. 1, Jan. 1959, pp. 44–50.

Neogi, A. N. and Jensen, J. R., "Wet Strength Improvement Via Fiber Surface Modification," *TAPPI*, vol. 63, No. 8, Aug. 1980, pp. 86–88.

Walecka, J. A., "An Investigation of Low Degree of Substitution Carboxymethylcelluloses," *TAPPI*, vol. 39, No. 7, Jul. 1956, p. 458–463.

Atack, D., Heitner, C. and Karnis, A., "Ultra–High Yield Pulping of Eastern Black Spruce, Part 2," *Svensk Papperstidning*, Nr. 5 (1980), pp. 133–141.

Heitner, C., Atack, D., and Karnis, A., "Ultra–High Yield Pulping of Eastern Black Spruce, Part 3. Interstage Sulfonation," *Svensk Papperstidning*, Jun. 1982, pp. R 78–R 86.

*Primary Examiner*—Gary L. Kunz
*Assistant Examiner*—Everett White
*Attorney, Agent, or Firm*—John R. Schenian

[57] ABSTRACT

Disclosed is a water-swellable, water-insoluble sulfonated cellulose having improved absorption properties. One embodiment of the present invention concerns a water-swellable, water-insoluble sulfonated cellulose having an average degree of sulfonic group substitution from about 0.2 to about 0.5 that exhibits an initial Absorbency Under Load value of at least about 8 grams per gram. The sulfonated cellulose may be used in disposable absorbent products.

21 Claims, No Drawings

SULFONATED CELLULOSE HAVING IMPROVED ABSORBENT PROPERTIES

BACKGROUND OF THE INVENTION

1. Field of the Invention

The present invention relates to sulfonated cellulose having improved absorbent properties. Specifically, the present invention relates to sulfonated cellulose having an improved ability to absorb liquid while under an external pressure.

2. Description of the Related Art

The use of water-swellable, generally water-insoluble absorbent materials, commonly known as superabsorbents, in disposable absorbent personal care products is known. Such absorbent materials are generally employed in absorbent products such as diapers, training pants, adult incontinence products, and feminine care products in order to increase the absorbent capacity of such products while reducing their overall bulk. Such absorbent materials are generally present in absorbent products in a fibrous matrix, such as a matrix of wood pulp fluff. A matrix of wood pulp fluff generally has an absorbent capacity of about 6 grams of liquid per gram of fluff. The superabsorbent materials generally have an absorbent capacity of at least about 10, preferably of about 20, and often of up to 100 times their weight in water. Clearly, incorporation of such absorbent materials in personal care products can reduce the overall bulk while increasing the absorbent capacity of such products.

A wide variety of materials has been described for use as absorbent materials in personal care products. Such materials include natural-based materials such as agar, pectin, gums, carboxyalkyl starch, and carboxyalkyl cellulose, as well as synthetic materials such as polyacrylates, polyacrylamides, and hydrolyzed polyacrylonitdle. While the natural-based absorbent materials are known for use in personal care products, they have not gained wide usage in such products. The natural-based absorbent materials have not gained wide usage in personal care products, at least in part, because their absorbent properties are generally inferior compared to the synthetic absorbent materials, such as the polyacrylates. Specifically, many of the natural-based materials tend to form soft, gelatinous masses when swollen with a liquid. When employed in absorbent products, the presence of such soft gelatinous masses tends to prevent the transport of liquid within the fibrous matrix in which the absorbent materials are incorporated. This phenomenon is known as gel-blocking. Once gel-blocking occurs, subsequent insults of liquid cannot be efficiently absorbed by the product, and the product tends to leak. Further, many of the natural-based materials exhibit poor absorption properties, particularly when subjected to external pressures.

In contrast, the synthetic absorbent materials are often capable of absorbing large quantities of liquid while maintaining a generally stiff, non-mucilaginous character. Accordingly, the synthetic absorbent materials can be incorporated in absorbent products while minimizing the likelihood of gel-blocking.

It is, therefore, desirable to develop and produce a natural-based, highly absorbent material having absorptive properties similar to the synthetic, highly absorptive materials and which, thus, is suitable for use in personal care absorbent products.

SUMMARY OF THE INVENTION

In one aspect, the present invention concerns a water-swellable, water-insoluble sulfonated cellulose. The sulfonated cellulose is characterized in that it exhibits desired absorbent properties.

One embodiment of the present invention concerns a water-swellable, water-insoluble sulfonated cellulose having an average degree of sulfonic group substitution from about 0.2 to about 0.5 that exhibits an initial Absorbency Under Load value of at least about 8 grams per gram.

Another embodiment of the present invention concerns a water-swellable, water-insoluble sulfonated cellulose having an average degree of sulfonic group substitution from about 0.2 to about 0.5 that exhibits an initial Free Swell value of at least about 10 grams per gram.

Another embodiment of the present invention concerns a water-swellable, water-insoluble sulfonated cellulose having an average degree of sulfonic group substitution from about 0.2 to about 0.5 that exhibits an initial Centrifuge Retention Capacity value of at least about 8 grams per gram.

In another aspect, the present invention concerns a disposable absorbent product comprising a water-swellable, water-insoluble sulfonated cellulose that exhibits desired absorbent properties.

In one embodiment of the present invention, a disposable absorbent product comprises a liquid-permeable topsheet, a backsheet attached to the topsheet, and an absorbent structure positioned between the topsheet and the backsheet wherein the absorbent structure comprises a water-swellable, water-insoluble sulfonated cellulose that has an average degree of sulfonic group substitution from about 0.2 to about 0.5 and that exhibits an initial Absorbency Under Load value of at least about 8 grams per gram.

DETAILED DESCRIPTION OF THE PREFERRED EMBODIMENT

It has now been discovered that cellulose fiber can be modified by sulfonation to provide the absorbent properties desired to use the sulfonated cellulose in, for example, disposable absorbent products. In accordance with this invention, the sulfonation of cellulose fibers to an effective degree of sulfonic group substitution results in significant and unexpected improvements in the absorbent properties of the sulfonated cellulose.

As used herein, a sulfonated cellulose is intended to refer to a hydroxy sulfonic cellulose in which both the sulfur atom of a sulfonic group and an hydroxyl group are directly attached to a carbon atom on the cellulose chain. The sulfonic group may generally be present in the acid form or in the neutralized or salt form. The hydroxy sulfonic acid functionality can generally be attached to any or all of the carbon atoms at the 2, 3, or 6 positions of cellulose or any combinations thereof. The carbon atoms at the 2, 3, or 6 positions of cellulose which am not substituted with hydroxy sulfonic acid can generally have either an aldehyde functionality or an hydroxyl functionality or any combinations thereof. Representative structures of sulfonated cellulose include, but are not limited to, the following:

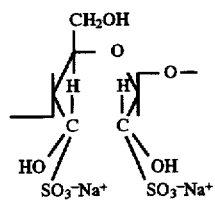

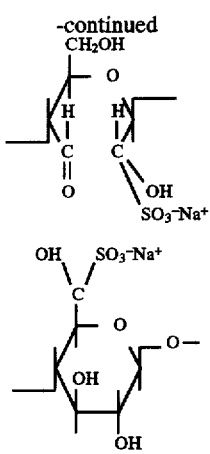

As such, the sulfonated cellulose of the present invention differs from other sulfur containing cellulose compounds in which the sulfur atom is indirectly connected to a carbon atom on the cellulose chain as, for example, in the case of cellulose alkyl sulfonates.

As used herein, "sulfonated cellulose" is not to be confused with "sulfonated pulp," the latter being the basis for the many varieties of sulfite pulping processes and most of the chemithermomechanical pulping processes. When sulfonating pulp, it is the lignin portion of the pulp that is sulfonated rather than sulfonation of the cellulose portion. Sulfonation of lignin serves to soften the lignin and/or make it soluble under suitable conditions in the form of sulfonated lignin or a ligno-sulfonate. In the case of chemithermomechanical pulping or its variations, the objective of the sulfonation has been to soften the lignin by sulfonation so that individual fibers can be separated from the mass with minimal damage to the fibers. The fiber separation is accomplished by mechanical means with thermal assistance to the sulfonation in softening the lignin binding individual fibers together. No attempt is made to dissolve or remove the lignin. In full chemical pulping by the sulfite process or one of its variations, the lignin is sulfonated under suitable conditions so that the lignin is dissolved and removed from the fiber as a ligno-sulfonate.

The sulfonated cellulose of the present invention can be characterized by an average degree of sulfonic group substitution of from about 0.2 to about 0.5, more specifically from about 0.225 to about 0.475, and still more specifically from about 0.24 to about 0.45. As used herein, the "average degree of sulfonic group substitution" is the average moles of sulfonic groups per mole of glucose unit in the cellulose. The maximum degree of sulfonic group substitution that can be obtained is 3 when all hydroxyl groups in the glucose residue are oxidized to aldehyde and subsequently converted to sulfonates.

When sulfonated cellulose has an average degree of sulfonic group substitution within the range of from 0 to less than about 0.2, the sulfonated cellulose has been found to generally be water insoluble but does not exhibit the absorbency properties desired in the present invention. When sulfonated cellulose has an average degree of sulfonic group substitution greater then about 0.5, the sulfonated cellulose has been found to generally be water soluble and also does not exhibit the absorbency properties desired in the present invention. However, one skilled in the art will appreciate that other characteristics, such as the actual pattern of sulfonic group substitution on the cellulose, may also have an effect on the water-solubility and the absorbency properties of the sulfonated cellulose.

Cellulose suitable for use in the present invention is generally water insoluble and not highly water swellable prior to oxidation and subsequent sulfonation of the cellulose to provide the sulfonated cellulose with the desired absorbency characteristics as disclosed herein. After such treatment to provide the sulfonated cellulose with the desired absorbency characteristics, the sulfonated cellulose will generally be water swellable and water insoluble.

As used herein, a material will be considered to be water soluble when it substantially dissolves in excess water to form a solution, thereby losing its initially particulate form and becoming essentially molecularly dispersed throughout the water solution. As a general rule, a water-soluble sulfonated cellulose will be free from a substantial degree of crosslinking, as crosslinking tends to render the sulfonated cellulose water insoluble.

As used herein, the term "water-swellable, water-insoluble" is meant to refer to a material that, when exposed to an excess of water, swells to its equilibrium volume but does not dissolve into the solution. As such, a water-swellable, water-insoluble material generally retains its original identity or physical structure, but in a highly expanded state, during the absorption of the water and, thus, must have sufficient physical integrity to resist flow and fusion with neighboring particles.

Sulfonated cellulose may generally have a wide range of molecular weights. Sulfonated cellulose having a relatively high molecular weight is often beneficial for use in the present invention. Nonetheless, a wide range of molecular weights is suitable for use in the present invention. It is generally most convenient to express the molecular weight of a sulfonated cellulose in terms of its viscosity in a 1.0 weight percent aqueous dispersion at 25° C. Sulfonated cellulose suitable for use in the present invention will suitably have a viscosity in a 1.0 weight percent aqueous dispersion at 25° C. of from about 100 centipoise (100 mPa.s) to about 100,000 centipoise (100,000 mPa.s), more suitably from about 150 centipoise (150 mPa.s) to about 90,000 centipoise (90,000 mPa.s), and most suitably from about 200 centipoise (200 mPa.s) to about 80,000 centipoise (80,000 mPa.s).

Cellulosic materials with a wide range of degree of polymerization are generally suitable for making the sulfonated cellulose materials of the present invention. It is often beneficial to use cellulosic materials with a relatively high degree of polymerization. Cellulosic material suitable for use in the present invention will suitably have a degree of polymerization greater than about 100, more suitably greater than about 500, and most suitably greater than about 1000.

It has been found to be possible to produce an improvement in absorbent properties in sulfonated cellulose over a wide range of molecular weights. While high molecular weight sulfonated celluloses are generally preferred, it is important that improvements in absorbent properties in low molecular weight sulfonated cellulose can also be achieved. This is because aqueous dispersions of high molecular weight sulfonated cellulose generally exhibit a higher viscosity as compared to an aqueous dispersion containing the same concentration of low molecular weight sulfonated celluloses. For reasons of efficiency, it is often desirable to form an aqueous dispersion comprising the highest concentration of sulfonated cellulose possible while still being able to effectively work with the aqueous dispersion.

In one embodiment of the present invention, the sulfonated cellulose has the ability to absorb a liquid while the sulfonated cellulose is under an external pressure or load, herein referred to as Absorbency Under Load (AUL). Synthetic polymeric materials, such as polyacrylates, having a generally high ability to absorb a liquid while under a load, have been found to minimize the occurrence of gel-blocking when incorporated in absorbent products. The method by which the Absorbency Under Load is determined is set forth below in connection with the examples. The Absorbency Under Load values determined as set forth below and reported herein refer to the amount in grams of an aqueous solution, containing 0.9 weight percent sodium chloride, a gram of a material can absorb in 60 minutes under a load of about 0.3 pound per square inch (psi). As a general rule, it is desired that the sulfonated cellulose of the present invention has an initial Absorbency Under Load value, for a load of about 0.3 psi, of at least about 8, beneficially of at least about 10, more beneficially of at least about 12, suitably of at least about 14, more suitably of at least about 16, and up to about 50 grams per gram. As used herein, the term "initial Absorbency Under Load value" is meant to refer to that Absorbency Under Load value exhibited by a material as measured within about one day after preparation of the material while the material is stored at ambient conditions, such as at about 24° C. and between about 30 to about 60 percent relative humidity.

In one embodiment of the present invention, the sulfonated cellulose has the ability to absorb a liquid while the sulfonated cellulose is under a negligible external pressure or load, herein referred to Free Swell (FS). The method by which the Free Swell is determined is set forth below in connection with the examples. The Free Swell values determined as set forth below and reported herein refer to the amount in grams of an aqueous solution, containing 0.9 weight percent sodium chloride, a gram of a material can absorb in 60 minutes under a load of about 0.01 pound per square inch (psi). As a general rule, it is desired that the sulfonated cellulose has an initial Free Swell value of at least about 10, beneficially of at least about 12, suitably of at least about 14, more suitably of at least about 16, and up to about 50 grams per gram. As used herein, the term "initial Free Swell value" is meant to refer to that Free Swell value exhibited by a material as measured within about one day after preparation of the material while the material is stored at ambient conditions, such as at about 24° C. and between about 30 to about 60 percent relative humidity.

In one embodiment of the present invention, the sulfonated cellulose has the ability to retain a liquid within its structure while the sulfonated cellulose is subjected to a centrifugal force, herein referred to as Centrifuge Retention Capacity (CRC). The method by which the Centrifuge Retention Capacity is determined is set forth below in connection with the examples. The Centrifuge Retention Capacity values determined as set forth below and reported herein refer to the amount in grams of an aqueous solution, containing 0.9 weight percent sodium chloride, a gram of a material can retain after absorbing the aqueous saline solution for about 30 minutes under essentially no load and then being centrifuged for about 3 minutes at about 263.5 times the gravitational force. As a general rule, it is desired that the sulfonated cellulose has an initial Centrifuge Retention Capacity value of at least about 8, beneficially of at least about 10, more beneficially of at least about 12, suitably of at least about 14, more suitably of at least about 16, and up to about 50 grams per gram. As used herein, the term "initial Centrifuge Retention Capacity value" is meant to refer to that Centrifuge Retention Capacity value exhibited by a material as measured within about one day after preparation of the material while the material is stored at ambient conditions, such as at about 24° C. and between about 30 to about 60 percent relative humidity.

In one embodiment of the present invention, the sulfonated cellulose has the ability to retain a liquid within its structure for a period of time while the sulfonated cellulose is subjected to a drying temperature, herein referred to as Water Affinity. The method by which the Water Affinity is determined is set forth below in connection with the examples. The Water Affinity values determined as set forth below and reported herein refer to the amount of time, in minutes, a gram of a material takes to be dried to a constant weight at a temperature of about 40° C. after the material has been allowed to absorb aqueous saline solution, containing 0.9 weight percent sodium chloride, for about 30 minutes under no load and is centrifuged for about 3 minutes at about 263.5 times the gravitational force. As a general rule, it is desired that the sulfonated cellulose has an initial Water Affinity value of at least about 300 minutes, beneficially of at least about 400 minutes, more beneficially of at least about 600 minutes, suitably of at least about 800 minutes, more suitably of at least about 1000 minutes, and up to about 10,000 minutes. As used herein, the term "initial Water Affinity value" is meant to refer to that Water Affinity value exhibited by a material as measured within about one day after preparation of the material while the material is stored at ambient conditions, such as at about 24° C. and between about 30 to about 60 percent relative humidity.

It has been found that the sulfonated cellulose of the present invention may be prepared by a simple process. In general, the method of making sulfonated cellulose fiber comprises the steps of (a) oxidizing cellulose fiber with an oxidizing agent to form aldehydo cellulose; and (b) sulfonating the oxidized cellulose with a sulfonation agent to form sulfonated cellulose. The chemical reactions taking place in carrying out the method of this invention can be symbolically shown as follows:

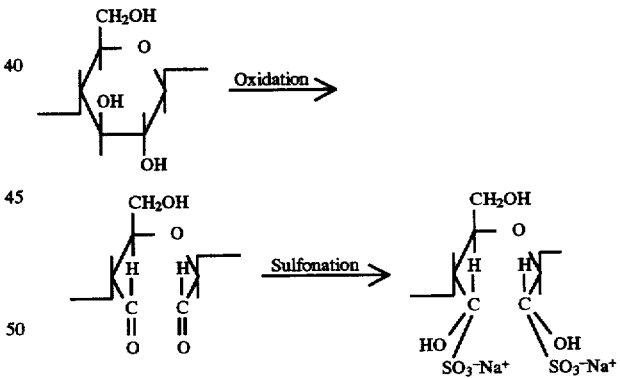

With regard to the oxidation reaction, there are a great many ways in which the chain units in cellulose can be oxidized. However, most oxidants are unspecific in their mode of attack. Suitable oxidants for purposes of this invention include, without limitation, sodium metaperiodate, sodium paraperiodate, periodic acid, sodium hypochlorite, hydrogen peroxide, ozone, potassium dichromate, potassium permanganate, and sodium chlorite. Periodate ions react with the cellulose without destroying its fibrous nature and result primarily in the oxidative scission of 1,2- diols to primarily produce dialdehyde oxycellulose under proper conditions. For this reason the preferred oxidizing agents are the periodates, such as sodium metaperiodate ($NaiO_4$).

The temperature of the oxidation reaction can suitably be from about 20° C. to about 55° C., more suitably from about 30° C. to about 50° C., and most suitably from about 35° C. to about 40° C. At temperatures below about 20° C., the oxidation reaction generally proceeds too slowly to be practical. At temperatures greater than about 55° C., the oxidation of cellulose generally results in a degradation of the cellulose and also causes nonuniformity of the substitution.

The pH of the oxidation reaction can suitably be from about 2 to about 7, more suitably from about 3 to about 6.5, and most suitably from about 3 to about 5. When using sodium metaperiodate, for example, it is generally desirable to use a pH that is between about 3 to about 4.6, since at a higher pH, the sodium metaperiodate is generally converted to insoluble paraperiodate.

If sodium metaperiodate is used as the oxidation agent, the upper concentration of sodium metaperiodate is generally limited by its solubility in water, which is about 14.44 grams per 100 milliliters at 25° C. The maximum concentration of sodium metaperiodate which can therefore be achieved is about 0.67M. At concentrations of sodium metaperiodate below about 0.005M, the rate of reaction is generally too slow for the oxidation process to be economically feasible. Suitable concentrations of sodium metaperiodate are from about 0.01M to about 0.5M. At higher concentrations, although the oxidation reaction will proceed faster toward the desired degree of substitution, the shorter treatment time is likely to result in non-uniformity of the substitution.

With regard to the sulfonation reaction, suitable sulfonation reagents include, without limitation, alkali bisulfite, such as sodium bisulfite, and a combination of sodium hydroxide and sulfur dioxide. A preferred reagent is sodium bisulfite ($NaHSO_3$). The concentration of sulfonation reagent is generally not critical provided there is an excess over the stoichiometric amount required.

When using sodium bisulfite as the sulfonation agent, the concentration of the sodium bisulfite is suitably from about 1 to about 140 weight percent, more suitably from about 60 to about 80 weight percent, based on the weight of the cellulose fiber.

The temperature of the sulfonation reaction is suitably from about 25° C. to about 90° C. or greater, more suitably from about 25° to about 35° C.

The pH of the sulfonation reaction is suitably from about 3 to about 4.5. Although the sulfonation reaction generally proceeds faster at lower pH levels, sulfur dioxide will be lost unless the reaction is carried out under pressure. Also, at high temperatures and acidic pH, cellulose is likely to undergo hydrolytic degradation.

A suitable method of making sulfonated cellulose is to oxidize cellulose with sodium metaperiodate at a concentration above about 0.2M for about 3 hours at about 35° C. The aldehydo cellulose or dialdehyde oxycellulose thus produced is then suitably washed with water to remove any unreacted sodium metaperiodate and any soluble reaction products. The oxidized cellulose fibers are then reacted with a greater than about 2 percent aqueous solution of sodium bisulfite at ambient temperature or higher for about 2 hours at a pH of about 4.5. The product is then washed again to remove unreacted bisulfite and any soluble reaction products and dried by conventional means for shipment or storage.

The method of preparation of sulfonated cellulose is shown, for example, in U.S. Application Ser. No. 08/250, 186 by Ram Shet, filed May 27, 1994, the disclosure of which is hereby incorporated in its entirety by reference.

The oxidation and subsequent sulfonation of cellulose can be carried out on a wide variety of raw materials including celluloses derived from both woody and non-woody plants, coniferous as well as deciduous trees, and by a variety of pulping processes including kraft, soda, a variety of sulfite processes, and chemithermomechanical pulping. Secondary fiber obtained by recycling waste paper would also be suitable as a raw material for oxidation and sulfonation.

The oxidation/sulfonation can also be carded out on any of the above-mentioned celluloses that have been mechanically refined prior to the oxidation/sulfonation process. When used as a pretreatment, refining serves to bring about external and internal fibrillation of the cellulose fibers. This generally increases the surface area of the fibers and also increases accessibility of the fibrils and cellulose chains to oxidation/sulfonation.

Cellulose is generally known to be a highly crystalline material. The degree of crystallinity generally depends on the source of the cellulose and its processing history. The highly-ordered crystalline structures and the less-ordered amorphous areas generally have different accessibilities to oxidizing and sulfonating agents. The result of this difference in accessibility is that the amorphous areas and surface of crystallites are, in the case of reaction with an oxidizing agent, generally oxidized first and heaviest, whereas the highly crystalline areas are oxidized last and least. Swelling of the cellulose improves the accessibility of the oxidizing agent into the crystalline areas and facilitates the oxidation. Any other process that would increase accessibility, including the use of never-dried pulp, would also generally be beneficial. In general, it is observed that the crystallinity of the sulfonated cellulose decreases with an increasing degree of sulfonic group substitution.

In one embodiment of the present invention, the sulfonated cellulose has a crystallinity effective to result in the sulfonated cellulose exhibiting the desired absorbent properties described herein. The method by which the crystallinity is determined is set forth below in connection with the examples. The Crystallinity values determined as set forth below and reported herein refer to the amount of highly-ordered structure present in the cellulose structure, as compared to the less-ordered, amorphous area of the cellulose. As a general rule, it is desired that the sulfonated cellulose has a Crystallinity value of less than about 50 percent, beneficially of less than about 40 percent, more beneficially of less than about 30 percent, suitably of less than about 20 percent, and more suitably of less than about 10 percent.

After preparation of a sulfonated cellulose, the sulfonated cellulose is desirably recovered from the reaction mixture in which it was prepared. Any method of recovering the sulfonated cellulose from the reaction mixture, without unacceptably deteriorating the absorption properties of the sulfonated cellulose, is suitable in the present invention. Examples of such methods include evaporative drying, freeze drying, precipitation, critical point drying, and the like.

As used herein, recovery of the sulfonated cellulose from a reaction mixture is meant to represent that substantially all of the water and, if present, nonsolvent is separated from the sulfonated cellulose prior to additional treatment steps. It will be appreciated however that, even after removal of substantially all of the water and nonsolvent, a small amount of water and nonsolvent may remain entrapped within the structure of the sulfonated cellulose. The amount of water and nonsolvent remaining entrapped within the structure of the sulfonated cellulose will typically depend on the method and conditions under which the sulfonated cellulose is prepared and then recovered. Beneficially, less than about 15 weight percent, suitably less than about 10 weight percent, and more suitably less than about 7 weight percent, based on the total weight of the sulfonated cellulose, water, and nonsolvent, will be the water and nonsolvent remaining entrapped within a recovered sulfonated cellulose.

Suitably, the sulfonated cellulose is recovered from the mixture with evaporative drying. As a general rule, the sulfonated cellulose can be recovered by evaporative drying at a temperature within the range of from about 10° C. to about 100° C., suitably from about 40° C. to about 60° C. Naturally, higher temperatures can be employed if the mixture is placed under pressure. Lower temperatures can be employed if the mixture is placed under a vacuum.

Other methods of recovery include precipitation in which a precipitating agent, such as methanol, ethanol, isopropanol, or acetone, is added to the mixture to precipitate the sulfonated cellulose out of the mixture. The sulfonated cellulose can then be recovered by filtration. If precipitation is used to recover the sulfonated cellulose, it may be desirable to wash the recovered sulfonated cellulose to remove the precipitating agent.

Depending on the form in which the sulfonated cellulose is recovered, it may be necessary or desirable to alter the form of the sulfonated cellulose. For example, if evaporative drying is employed, the sulfonated cellulose may be recovered in the form of a film or sheet. It may be desirable to comminute the film or sheet material into particles or flakes of material.

The form of the recovered sulfonated cellulose desired will depend to a large extent on the use for which it is intended. When the sulfonated cellulose is intended for use in absorbent personal care products, it is generally desired that the sulfonated cellulose be in the form of a discrete particle, fiber or flake. When in the form of a particle, it is generally desired that the particle have a maximum cross-sectional dimension beneficially within the range from about 50 micrometers to about 2,000 micrometers, suitably within the range from about 100 micrometers to about 1,000 micrometers, and more suitably within the range from about 300 micrometers to about 600 micrometers.

The properties of sulfonated cellulose of this invention would enable it to function as a thickener, flow-control agent, encapsulant, water binder, suspending agent, protective colloid, flocculant, film former or drag reducing agent with a broad range of potential applications in food, water treatment, oil recovery, agriculture, cosmetics, pharmaceuticals, adhesives, paper and building materials.

In particular, the sulfonated cellulose of the present invention is suitable for use in disposable absorbent products such as personal care products, such as diapers, training pants, baby wipes, feminine care products, adult incontinent products; and medical products, such as wound dressings or surgical capes or drapes. When the sulfonated cellulose of the present invention is intended for use in disposable absorbent products, it is typically desired that the sulfonated cellulose have a generally neutral or slightly acid character.

In one embodiment of the present invention, a disposable absorbent product is provided, which disposable absorbent product comprises a liquid-permeable topsheet, a backsheet attached to the topsheet, and an absorbent structure positioned between the topsheet and the backsheet wherein the absorbent structure comprises the sulfonated cellulose of the present invention, wherein the sulfonated cellulose exhibits desired absorbent properties.

Those skilled in the art will recognize materials suitable for use as the topsheet and backsheet. Exemplary of materials suitable for use as the topsheet are liquid-permeable materials, such as spunbonded polypropylene or polyethylene having a basis weight of from about 15 to about 25 grams per square meter. Exemplary of materials suitable for use as the backsheet are liquid-impervious materials, such as polyolefin films, as well as vapor-pervious materials, such as microporous polyolefin films.

Disposable absorbent products, according to all aspects of the present invention, are generally subjected during use to multiple insults of a body liquid. Accordingly, the disposable absorbent products are desirably capable of absorbing multiple insults of body liquids in quantities to which the absorbent products and structures will be exposed during use. The insults are generally separated from one another by a period of time.

TEST METHODS

Absorbency Under Load

The Absorbency Under Load (AUL) is a test which measures the amount in grams of an aqueous solution, containing 0.9 weight percent sodium chloride, a gram of a material can absorb in 60 minutes under a load of about 0.3 pound per square inch.

A sample cup consists of a plastic cylinder having a 1 inch inside diameter and an outside diameter of 1.25 inches. The bottom of the sample cup is formed by adhering a 100 mesh metal screen having 150 micron openings to the end of the cylinder by heating the screen above the melting point of the plastic and pressing the plastic cylinder against the hot screen to melt the plastic and bond the screen to the plastic cylinder.

To carry out the test, a 0.160 gram sample of the absorbent material, which has been sieved to a particle size between 300 and 600 microns, is placed into the sample cup. The sample is then covered with a plastic spacer disc, weighing 4.4 grams and having a diameter of about 0.995 inch, which serves to protect the sample from being disturbed during the test and also to uniformly apply a load on the entire sample. A 100 gram weight is then placed on top of the spacer disc, thereby applying a load of about 0.3 pound per square inch to the sample material. The sample cup, with material sample, spacer disc, and 100 gram weight, is then weighed to obtain its dry weight.

The sample cup is placed in a Petri dish. A sufficient amount of saline solution is added to the Petri dish (50–100 milliliters) to begin the test. The sample cup is kept in the Petri dish for about 60 minutes after which it is removed, lightly blotted with a paper towel to remove any free water droplets adhering to the sample cup, and then weighed.

The AUL is calculated by determining the weight difference between the sample cup before and after the test, the weight difference being the amount of solution absorbed by the material sample. The weight of saline solution absorbed after about 60 minutes is the AUL value expressed as grams saline solution absorbed per gram of sample material.

Free Swell Capacity

The Free Swell Capacity (FS) is a test which measures the ability of an absorbent material to absorb a liquid (such as a 0.9 weight percent solution of sodium chloride in distilled water) while under a negligible (about 0.01 psi or less) applied load or restraining force.

The Free Swell Capacity of a sample material is determined in a manner similar to the test method used to determine Absorbency Under Load (for a load of about 0.3 psi), with the exception that the 100 gram weight is not placed on the spacer disc in the sample cup. The spacer disc is used to prevent substantial movement of the sample material in the sample cup and exerts a load of about 0.01 psi onto the sample material. The weight of 0.9 weight percent saline solution absorbed after about 60 minutes is the Free Swell value expressed as grams of saline solution absorbed per gram of sample material.

Centrifuge Retention Capacity

The Centrifuge Retention Capacity (CRC) is a test which measures the ability of an absorbent material to retain an absorbed liquid after being subjected to a centrifugal force for a period of time.

Stock teabag material is cut into a 3 inch by 5 inch rectangle and folded in half to form a 2.5 inch by 3 inch rectangle with the sealable face inward. Two of the three open sides are heat sealed with the inside edge of the seal about 0.25 inch from the edge. About 0.2 gram of sample material is placed into a preweighed teabag, and the open end of the teabag is heat sealed. The teabag is placed in a pan of a 0.9 weight percent solution of sodium chloride in distilled water for about 30 minutes, removed, and then centrifuged for about 3 minutes at 263.5 times the gravitational force. A blank test is also run by centrifuging under similar conditions an empty teabag which had also been placed in the aqueous saline solution. The weight of saline retained per gram of dry sample material after centrifugation is calculated from the data obtained, and this is expressed as the Centrifuge Retention Capacity value in terms of grams of aqueous saline solution retained per gram of dry sample material.

Water Affinity

The Water Affinity is a test which measures the ability of an absorbent material to retain an absorbed liquid after being subjected to an elevated temperature for a period of time.

The Water Affinity of a sample material is determined in a manner similar to the test method used to determine Centrifuge Retention Capacity with the exception that, after the sample material is centrifuged, the sample material is further evaluated by placing it on a pan of a gravimetic moisture analyzer, commercially available from Sartorius Instruments, McGaw Park, Ill., under the designation MA50 gravimetic moisture analyzer, and heating the sample material at a temperature of about 40° C. to a constant weight. The weight of the sample was recorded continuously to determine the sample dryness. The time, in minutes, taken to dry the sample material to a constant weight at 40° C. is the Water Affinity value of the sample material.

Crystallinity

The Crystallinity of a cellulose material represents the highly-ordered structure of the cellulose as compared to the less-ordered, amorphous area of the cellulose. Determination of Crystallinity was done using wide angle x-ray diffraction measurements. Dry, fibrous sample material is placed in the sample holder of a diffractometer, commercially available from Philips Electronics, Schaumburg, Ill., under the designation PW-1710 diffractometer. The irradiated length of the sample was 12 millimeters. A CuKα (copper/potassium alpha) x-ray beam at about 45 kilovolts tube voltage and about 40 milliamps tube current was used to make the measurements. The diffraction pattern is recorded over the scattering angle (2θ) range of from about 2 to about 40 degrees. The degree of Crystallinity of the sample material is determined from the recorded diffraction pattern as the percentage ratio of the area under the crystalline peaks to the combined area of the amorphous halo and the crystalline peaks. The calculated value is reported as the Crystallinity value in percent.

Sulfonic Group Substitution

The sulfur content of a treated cellulose material may be determined by elemental sulfur analysis and may be expressed as a weight percent of the cellulose material. The sulfonic group substitution of a sulfonated cellulose material is 0.05 times the percent sulfur content. In addition to elemental sulfur analysis, energy dispersive x-ray analysis may be used to confirm the presence of sulfur in the sulfonated cellulose material.

EXAMPLES

Sulfonated cellulose material was obtained using a two step synthesis procedure. In the first step, cellulose fibers were oxidized with sodium metaperiodate to obtain dialdehyde cellulose. The dialdehyde cellulose from the first step was then treated with sodium bisulfite in a second step to obtain sulfonated cellulose material.

Example 1

About 25 grams of never-dried, bleached, northern softwood kraft pulp, at about 25 weight percent consistency, was dispersed in about 100 milliliters of anhydrous methanol for about 15 minutes, filtered, and dried overnight at about 22° C. and about 30 percent relative humidity.

Example 2

About three grams of sodium metaperiodate was dissolved in about 425 milliliters of distilled water in a 1 liter reaction kettle, and the pH of the solution was adjusted to about 4.0 using dilute sulfuric acid. The temperature of the solution was increased to about 38° C. About 100 grams of never-dried, bleached, northern softwood kraft pulp, at about 25 weight percent consistency, was added to the solution of sodium metaperiodate. The reaction kettle was shielded against exposure to light and the pulp slurry was reacted under a blanket of nitrogen for about 60 minutes. After completion of the oxidation reaction, the cellulose pulp was recovered by filtration. The recovered cellulose was washed thoroughly to remove any unreacted sodium metaperiodate and soluble reaction products using the following procedure. The filtered pulp was dispersed in about 400 milliliters of distilled water of pH 6.0, agitated for about 15 minutes and filtered. This pulp washing step was repeated 5 times. The pulp, after the final filtration, was obtained at a consistency of about 25 weight percent. The product obtained from the pulp oxidation step was dialdehyde cellulose.

The dialdehyde cellulose pulp obtained was slurried at about 22° C. in about 400 milliliters of distilled water containing about 5 grams of sodium bisulfite. The treatment of dialdehyde cellulose with sodium bisulfite was continued for 2 hours. At the end of the reaction, the slurry was filtered and the sulfonated cellulose was recovered. The sulfonated cellulose was dispersed again in distilled water at about pH 6.0.After standing for about 15 minutes, the sulfonated pulp was again filtered. This washing step was repeated 6 times to remove unreacted sodium bisulfite. The sulfonated pulp was then recovered. The sulfonated pulp was then dispersed in about 100 milliliters of anhydrous methanol for about 15 minutes, filtered, and dried at about 22° C. and about 30 percent relative humidity. The degree of substitution of the sulfonated cellulose obtained was determined by elemental analysis to be about 0.01. When the dried, sulfonated cellulose was soaked in 0.15M saline solution, it physically resembled the starting cellulose material (never-dried, bleached, northern softwood kraft pulp) that was similarly soaked in 0.15M saline solution.

Example 3

Substantially the same procedure in example 2 was used except the amount of sodium metaperiodate used in the oxidation reaction was about 30 grams and the oxidation was performed for a duration of about 15 minutes. The degree of substitution of the sulfonated cellulose obtained was determined by elemental sulfur analysis to be about 0.10. When the dried, sulfonated cellulose was soaked in 0.15M saline solution, it physically resembled the starting cellulose material (never-dried, bleached, northern softwood kraft pulp) that was similarly soaked in 0.15M saline solution.

Example 4

Substantially the same procedure in example 2 was used except the amount of sodium metaperiodate used in the oxidation reaction was about 30 grams, the oxidation reaction was performed for a duration of about 45 minutes, and the amount of sodium bisulfite used in the sulfonation step was about 10 grams. The degree of substitution of the sulfonated cellulose obtained was determined by elemental sulfur analysis to be about 0.175. The sulfonated cellulose fibers appeared to swell slightly on soaking in saline but, still, largely resembled the starting cellulose material, similarly soaked in saline in appearance.

Example 5

Substantially the same procedure in example 2 was used except the amount of sodium metaperiodate used in the oxidation reaction was about 30 grams, the oxidation reaction was performed for a duration of about 90 minutes, and the amount of sodium bisulfite used in the sulfonation step was about 15 grams. The degree of substitution of the sulfonated cellulose obtained was determined by elemental sulfur analysis to be about 0.250. The sulfonated cellulose fibers tended to swell significantly on soaking in saline and the fibers appeared translucent.

Example 6

Substantially the same procedure in example 2 was used except the amount of sodium metaperiodate used in the oxidation reaction was about 30 grams, the oxidation reaction was performed for a duration of about 100 minutes, and the amount of sodium bisulfite used in the sulfonation step was about 15 grams. The degree of substitution of the sulfonated cellulose obtained was determined by elemental sulfur analysis to be about 0.266. The sulfonated cellulose fibers swelled significantly on being soaked in saline and the fibers were transformed to a transparent gel-like material.

Example 7

Substantially the same procedure in example 2 was used except the amount of sodium metaperiodate used in the oxidation reaction was about 30 grams, the oxidation reaction was performed for a duration of about 150 minutes, and the amount of sodium bisulfite used in the sulfonation step was about 15 grams. The degree of substitution of the sulfonated cellulose obtained was determined by elemental sulfur analysis to be about 0.304. The sulfonated cellulose fibers swelled significantly in saline and were transformed to a transparent gel-like material.

Example 8

Substantially the same procedure in example 2 was used except the amount of sodium metaperiodate used in the oxidation reaction was about 30 grams, the oxidation reaction was performed for a duration of about 210 minutes, and the amount of sodium bisulfite used in the sulfonation step was about 20 grams. The degree of substitution of the sulfonated cellulose obtained was determined by elemental sulfur analysis to be about 0.430. The sulfonated cellulose fibers were transformed to a highly swollen, transparent gel-like mass on soaking in saline.

Example 9

Substantially the same procedure in example 2 was used except the amount of sodium metaperiodate used in the oxidation reaction was about 30 grams, the oxidation reaction was performed for a duration of about 240 minutes, and the amount of sodium bisulfite used in the sulfonation step was about 25 grams. The degree of substitution of the sulfonated cellulose obtained was determined by elemental sulfur analysis to be about 0.505. The sulfonated cellulose obtained dissolved readily in saline to form a solution.

Example 10

Substantially the same procedure in example 2 was used except the amount of sodium metaperiodate used in the oxidation reaction was about 30 grams, the oxidation reaction was performed for a duration of about 300 minutes, and the amount of sodium bisulfite used in the sulfonation step was about 25 grams. The degree of substitution of the sulfonated cellulose obtained was determined by elemental sulfur analysis to be about 0.541. The sulfonated cellulose obtained dissolved readily in saline to form a solution.

Example 11

About 25 grams of cotton flock, having a fiber length of about 0.2 to about 0.4 millimeter, and available from Vertipile, a Division of Claremont Flock Corporation, was dispersed in about 100 milliliters of anhydrous methanol for about 15 minutes, filtered, and dried overnight at about 22° C. and about 30 percent relative humidity.

Example 12

Substantially the same procedure in example 2 was used except: 25 grams of cotton flock having a fiber length of about 0.2 to about 0.4 millimeter was used in place of the never-dried, bleached, northern softwood kraft pulp, the amount of sodium metaperiodate used in the oxidation reaction was about 30 grams, and the oxidation was performed for a duration of about 15 minutes. The degree of substitution of the sulfonated cellulose obtained was determined by elemental sulfur analysis to be about 0.07. When the dried, sulfonated cellulose was soaked in 0.15M saline solution, it physically resembled the starting cellulose material (never-dried, bleached, northern softwood kraft pulp) that was similarly soaked in 0.15M saline solution.

Example 13

Substantially the same procedure in example 12 was used except the oxidation was performed for a duration of about 45 minutes. The degree of substitution of the sulfonated cellulose obtained was determined by elemental sulfur analysis to be about 0.12. When the dried, sulfonated cellulose was soaked in 0.15M saline solution, it physically resembled the starting cellulose material (never-dried, bleached, northern softwood kraft pulp) that was similarly soaked in 0.15M saline solution.

Example 14

Substantially the same procedure in example 12 was used except the oxidation reaction was performed for a duration of about 60 minutes and the amount of sodium bisulfite used in the sulfonation step was about 10 grams. The degree of substitution of the sulfonated cellulose obtained was determined by elemental sulfur analysis to be about 0.154. The dried, sulfonated cellulose fibers appeared to swell slightly on soaking in 0.15M saline but, still, largely resembled the starting cellulose material, similarly soaked in saline, in appearance.

Example 15

Substantially the same procedure in example 12 was used except the oxidation reaction was performed for a duration of about 120 minutes and the amount of sodium bisulfite used in the sulfonation step was about 10 grams. The degree of substitution of the sulfonated cellulose obtained was determined by elemental sulfur analysis to be about 0.176. The dried, sulfonated cellulose fibers appeared to swell slightly on soaking in 0.15M saline but, still, largely resembled the starting cellulose material, similarly soaked in saline, in appearance.

Example 16

Substantially the same procedure in example 12 was used except the oxidation reaction was performed for a duration of about 150 minutes and the amount of sodium bisulfite used in the sulfonation step was about 15 grams. The degree of substitution of the sulfonated cellulose obtained was determined by elemental sulfur analysis to be about 0.196. The dried, sulfonated cellulose fibers swelled significantly on being soaked in 0.15M saline and the fibers appeared translucent.

Example 17

Substantially the same procedure in example 12 was used except the oxidation reaction was performed for a duration of about 180 minutes and the amount of sodium bisulfite used in the sulfonation step was about 15 grams. The degree of substitution of the sulfonated cellulose obtained was determined by elemental sulfur analysis to be about 0.217. The dried, sulfonated cellulose fibers swelled significantly on being soaked in 0.15M saline and the fibers appeared translucent.

Example 18

Substantially the same procedure in example 12 was used except the oxidation reaction was performed for a duration of about 210 minutes and the amount of sodium bisulfite used in the sulfonation step was about 15 grams. The degree of substitution of the sulfonated cellulose obtained was determined by elemental sulfur analysis to be about 0.240. The dried, sulfonated cellulose fibers swelled significantly on being soaked in 0.15M saline and the fibers appeared translucent.

Example 19

Substantially the same procedure in example 12 was used except the oxidation reaction was performed for a duration of about 270 minutes and the amount of sodium bisulfite used in the sulfonation step was about 20 grams. The degree of substitution of the sulfonated cellulose obtained was determined by elemental sulfur analysis to be about 0.322. The dried, sulfonated cellulose fibers swelled significantly on being soaked in 0.15M saline and the fibers appeared translucent.

Example 20

Substantially the same procedure in example 12 was used except the oxidation reaction was performed for a duration of about 330 minutes and the amount of sodium bisulfite used in the sulfonation step was about 25 grams. The degree of substitution of the sulfonated cellulose obtained was determined by elemental sulfur analysis to be about 0.424. The dried, sulfonated cellulose fibers, when soaked in 0.15M saline, was transformed to a highly swollen, transparent gel-like material.

Example 21

Substantially the same procedure in example 12 was used except the oxidation reaction was performed for a duration of about 420 minutes and the amount of sodium bisulfite used in the sulfonation step was about 25 grams. The degree of substitution of the sulfonated cellulose obtained was determined by elemental sulfur analysis to be about 0.516. The sulfonated cellulose obtained dissolved readily in 0.15M saline to form a solution.

Each sample material was prepared for evaluation by dispersing in a Waring blender for about 15 seconds, sieving the material, and collecting the fraction having a particle size between about 300 to about 600 micrometers. The collected material was then evaluated for Absorbency Under Load, Free Swell Capacity, Centrifuge Retention Capacity, Water Affinity, and Crystallinity values according to the test methods described herein. The respective values for Examples 1–10 are reported in Table 1. The respective values for Examples 11–21 are reported in Table 2.

While the present invention has been described in terms of the specific embodiments described above, numerous equivalent changes and modifications will be clear to those skilled in the art. Accordingly, the specific examples set forth above are not intended to limit in any manner the scope of the invention as set forth in the appended claims.

TABLE 1

| Sample # | Degree of Sulfonic Group Substitution | Absorbency Under Load (g/g) | Free Swell Capacity (g/g) | Centrifuge Retention Capacity (g/g) | Water Affinity (minutes) | Crystallinity (%) |
| --- | --- | --- | --- | --- | --- | --- |
| 1* | 0 | 4.6 | 5.8 | 1.6 | 120 | 61 |
| 2* | 0.01 | 5.2 | 6 | 2.3 | 154 | 59 |
| 3* | 0.10 | 6.1 | 6.1 | 3.4 | 164 | 57 |
| 4* | 0.175 | 7.8 | 8.2 | 6.1 | 204 | 53 |
| 5 | 0.250 | 11.6 | 15.4 | 14.7 | 780 | 9 |
| 6 | 0.266 | 12.4 | 16.6 | 15.8 | 1034 | 6 |
| 7 | 0.304 | 13.8 | 18 | 17.4 | 1248 | 3.7 |
| 8 | 0.430 | 15.6 | 19.9 | 19.5 | 1580 | 1.0 |
| 9* | 0.505 | 0 | 0 | 0 | — | 0.6 |
| 10* | 0.541 | 0 | 0 | 0 | — | 0.6 |

*Not an example of the present invention

TABLE 2

| Sample # | Degree of Sulfonic Group Substitution | Absorbency Under Load (g/g) | Free Swell Capacity (g/g) | Centriguge Retention Capacity (g/g) | Water Affinity (minutes) | Crystallinity (%) |
| --- | --- | --- | --- | --- | --- | --- |
| 11* | 0 | 3.8 | 4.3 | 1.5 | 135 | 72 |
| 12* | 0.07 | 4.2 | 4.4 | 1.8 | 158 | 71 |
| 13* | 0.12 | 4.6 | 4.7 | 2.1 | 176 | 67 |
| 14* | 0.154 | 5.2 | 5.2 | 2.8 | 208 | 64 |
| 15* | 0.176 | 5.8 | 6.4 | 4.6 | 242 | 61 |
| 16* | 0.196 | 6.5 | 7.2 | 5.9 | 286 | 56 |
| 17 | 0.217 | 7.9 | 8.6 | 7.3 | 520 | 49 |
| 18 | 0.240 | 10.8 | 12.4 | 11.8 | 946 | 11 |
| 19 | 0.322 | 12.2 | 14.5 | 14.1 | 1468 | 7 |
| 20 | 0.424 | 14.4 | 16.1 | 15.9 | 1980 | 2 |
| 21* | 0.516 | 0 | 0 | 0 | — | 0.8 |

*Not an example of the present invention

What is claimed is:

1. A water-swellable, water-insoluble sulfonated cellulose, having an average degree of sulfonic group substitution from about 0.2 to about 0.5, that exhibits an initial Absorbency Under Load value of at least about 8 grams per gram, wherein the sulfonated cellulose comprises both a sulfur atom of a sulfonic group and a hydroxyl group directly attached to a carbon atom on the cellulose.

2. The sulfonated cellulose of claim 1 wherein the sulfonated cellulose has an average degree of sulfonic group substitution from about 0.225 to about 0.475.

3. The sulfonated cellulose of claim 2 wherein the sulfonated cellulose has average degree of sulfonic group substitution from about 0.24 to about 0.45.

4. The sulfonated cellulose of claim 1 wherein the sulfonated cellulose exhibits an initial Absorbency Under Load value of at least about 10 grams per gram.

5. The sulfonated cellulose of claim 4 wherein the sulfonated cellulose exhibits an initial Absorbency Under Load value of at least about 12 grams per gram.

6. A water-swellable, water-insoluble sulfonated cellulose, having an average degree of sulfonic group substitution from about 0.24 to about 0.45, that exhibits an initial Absorbency Under Load value of at least about 12 grams per gram, wherein the sulfonated cellulose comprises both a sulfur atom of a sulfonic group and a hydroxyl group directly attached to a carbon atom on the cellulose.

7. A water-swellable, water-insoluble sulfonated cellulose, having an average degree of sulfonic group substitution from about 0.2 to about 0.5, that exhibits an initial Free Swell value of at least about 10 grams per gram, wherein the sulfonated cellulose comprises both a sulfur atom of a sulfonic group and a hydroxyl group directly attached to a carbon atom on the cellulose.

8. The sulfonated cellulose of claim 7 wherein the sulfonated cellulose has an average degree of sulfonic group substitution from about 0.225 to about 0.475.

9. The sulfonated cellulose of claim 8 wherein the sulfonated cellulose has average degree of sulfonic group substitution from about 0.24 to about 0.45.

10. The sulfonated cellulose of claim 7 wherein the sulfonated cellulose exhibits an initial Free Swell value of at least about 12 grams per gram.

11. The sulfonated cellulose of claim 10 wherein the sulfonated cellulose exhibits an initial Free Swell value of at least about 14 grams per gram.

12. The sulfonated cellulose of claim 10 wherein the sulfonated cellulose exhibits an initial Centrifuge Retention Capacity value of at least about 12 grams per gram.

13. The sulfonated cellulose of claim 7 wherein the sulfonated cellulose exhibits an initial Centrifuge Retention Capacity value of at least about 10 grams per gram.

14. A water-swellable, water-insoluble sulfonated cellulose, having an average degree of sulfonic group substitution from about 0.24 to about 0.45, that exhibits an initial Free Swell value of at least about 16 grams per gram, wherein the sulfonated cellulose comprises both a sulfur atom of a sulfonic group and a hydroxyl group directly attached to a carbon atom on the cellulose.

15. A water-swellable, water-insoluble sulfonated cellulose, having an average degree of sulfonic group substitution from about 0.2 to about 0.5, that exhibits an initial Centrifuge Retention Capacity value of at least about 8 grams per gram, wherein the sulfonated cellulose comprises both a sulfur atom of a sulfonic group and a hydroxyl group directly attached to a carbon atom on the cellulose.

16. The sulfonated cellulose of claim 15 wherein the sulfonated cellulose has an average degree of sulfonic group substitution from about 0.225 to about 0.475.

17. The sulfonated cellulose of claim 16 wherein the sulfonated cellulose has average degree of sulfonic group substitution from about 0.24 to about 0.45.

18. A water-swellable, water-insoluble sulfonated cellulose, having an average degree of sulfonic group substitution from about 0.24 to about 0.45, that exhibits an initial Centrifuge Retention Capacity value of at least about 14 grams per gram, wherein the sulfonated cellulose comprises both a sulfur atom of a sulfonic group and a hydroxyl group directly attached to a carbon atom on the cellulose.

19. A water-swellable, water-insoluble sulfonated cellulose, having an average degree of sulfonic group substitution from about 0.2 to about 0.5, that exhibits an initial Absorbency Under Load value of at least about 10 grams per gram, an initial Free Swell value of at least about 12 grams per gram, and an initial Centrifuge Retention Capacity value of at least about 10 grams per gram, wherein the sulfonated cellulose comprises both a sulfur atom of a sulfonic group and a hydroxyl group directly attached to a carbon atom on the cellulose.

20. A disposable absorbent product comprising a liquid-permeable topsheet, a backsheet attached to the topsheet, and an absorbent structure positioned between the topsheet and the backsheet, wherein the absorbent structure comprises a water-swellable, water-insoluble sulfonated cellulose having an average degree of group substitution from about 0.2 to about 0.5 and exhibiting an initial Absorbency Under Load value of at least about 8 grams per gram, wherein the sulfonated cellulose comprises both a sulfur atom of a sulfonic group and a hydroxyl group directly attached to a carbon atom on the cellulose.

21. A disposable absorbent product comprising a liquid-permeable topsheet, a backsheet attached to the topsheet, and an absorbent structure positioned between the topsheet and the backsheet, wherein the absorbent structure comprises a water-swellable, water-insoluble sulfonated cellulose having an average degree of sulfonic group substitution from about 0.2 to about 0.5 and exhibiting an initial Absorbency Under Load value of at least about 10 grams per gram, an initial Free Swell value of at least about 12 grams per gram, and an initial Centrifuge Retention Capacity value of at least about 10 grams per gram, wherein the sulfonated cellulose comprises both a sulfur atom of a sulfonic group and a hydroxyl group directly attached to a carbon atom on the cellulose.

* * * * *